(12) United States Patent
Sato et al.

(10) Patent No.: US 6,444,597 B1
(45) Date of Patent: Sep. 3, 2002

(54) DENTAL PASTE-LIKE PORCELAIN

(75) Inventors: Takahiro Sato, 3-31-2, Yamatocho, Nakano-ku, Tokyo (JP); Keisuke Ikushima, Tokyo (JP)

(73) Assignee: Takahiro Sato, Tokyo (JP)

( * ) Notice: Subject to any disclaimer, the term of this patent is extended or adjusted under 35 U.S.C. 154(b) by 18 days.

(21) Appl. No.: 09/662,140

(22) Filed: Sep. 14, 2000

(30) Foreign Application Priority Data

Sep. 16, 1999 (JP) .......................................... 11-261427

(51) Int. Cl.$^7$ ........................ A61C 13/083; A61K 6/02; C04B 33/00
(52) U.S. Cl. ............................................ 501/20; 106/35
(58) Field of Search ............................... 106/35; 501/20

(56) References Cited

U.S. PATENT DOCUMENTS 5,679,144 A * 10/1997 Thiel et al. .................... 106/35

* cited by examiner

*Primary Examiner*—C. Melissa Koslow
(74) *Attorney, Agent, or Firm*—Oblon, Spivak, McClelland, Maier & Neustadt, P.C.

(57) ABSTRACT

A dental paste-like porcelain is disclosed, including a mixture in a paste-like state of from 7 to 45 parts by weight of a binder comprising a synthetic and/or natural, hydrophilic group-containing polymeric material dissolved in one or two or more organic solvents selected from a dihydric or trihydric alcohol, a hydroxyl group-remaining ether and a hydroxy(meth) acrylate, and/or water and having a viscosity, as measured at a constant temperature of 23° C. and at a conversion constant of $1.61 \times 10^4$ under the conditions that a revolution number is 1 rpm, of from 50,000 to 1,500,000 cps, andaporcelain powder as a remainder, with a total amount being 100 parts by weight. The dental paste-like porcelain according to the invention does not require a condensation procedure. Accordingly, even a beginner can easily carry out the porcelain application of prostheses over a wide range including from a single crown to a bridge, without necessity of the skill. Further, since the dental paste-like porcelain of the present invention is a paste having no porosity incorporated therein and is stable during the present preservation over a long period of time. Moreover, it is hardly dried and hardened during the use and enables to grasp the shade.

10 Claims, No Drawings

DENTAL PASTE-LIKE PORCELAIN

BACKGROUND OF THE INVENTION

1. Field of the Invention

The present invention relates to a dental paste-like porcelain that is suitably used as a dental porcelain, such as a porcelain for laminated veneers, a porcelain for metal-ceramic restorations, and a porcelain for all ceramics, which are used for the preparation of artificial teeth and prosthetic restoration and in particular, require a special application technique by manual works of a dental technician.

2. Description of the Conventional Art

As the current of dental materials that have been put on the market in recent years, there are made various devices for shortening the time of an operation of the dental remedy or dental technique and making the operation easy. Further, machines for preparing metallic or ceramic tooth crowns, inlays, and veneers (one of techniques of the esthetic dentistry in which they are used upon being stuck onto a facial surface of a tooth) without needs of manual works through cutting processing by computer control typified by CAD/CAM (computer-aided design/computer-aided manufacturing) have begun to be put on the market. Thus, the dental technical works are being surely shortened in terms of time and made simple.

However, with respect to a porcelain application, which a dental technician who is mainly engaged in the dental laboratory works carries out, since a porcelain powder is in a sand-like state, it is poor in shaping properties. In addition to this, since water is used as a temporary binder with the porcelain powders, the buildup procedure is more difficult. And, in order to remove an excess of the water used as the binder during the buildup procedure, a condensation is carried out by imparting vibration. In the case where a person who is engaged in the dental laboratory works (the person being sometimes referred to as "person engaged," hereinafter) is a beginner, the fired porcelain is liable to be deformed.

In particular, in the case where a long-span bridge or the like is prepared as a large-sized prosthesis, the porcelain application range is wide, and therefore, a possibility of occurrence of deformation of the fired prosthesis is high. Thus, it has been said that careful dental laboratory works for an excess of time are necessary. For this reason, of the persons engaged, only skilled seniors called as "ceramist" have been engaged in the application of the porcelain.

While such circumstances have continued, there is recently made an attempt to overcome the foregoing problems. In this attempt, a forming liquid containing a small amount of an organic material as the temporary binder with the porcelain powders, which imparts a predetermined shape more easily than distilled water, i.e., is good in shaping properties, is used, thereby making the porcelain application works easy to a slight extent. However, even in this attempt, there is no change in the matter that a condensation procedure is necessary for making the porcelain densely packed and removing the excess water after the buildup procedure in a later stage. And it is considered that the long-span porcelain application still requires a high-grade skillful technique.

In the case where a beginner undergoes the porcelain application with a commercially available porcelain, one of problems to be encountered is shade matching. That is, in the beginning stage, the buildup works themselves are considerably difficult. And, even when the buildup is carried out, in many cases, a color of the resulting prosthesis does not become an intended one. On the other hand, a paste-like resin material for crown and bridge that is used for the same purpose as a tooth-color crown material is easy for the buildup, whereby even a beginner can carry out the buildup including shade matching without any difficulty. This is because, although, in the porcelain application work, a step for firing at a high temperature of from about 650 to 1,000° C. after the buildup is included, the resin material for crown and bridge can be used as it stands without including such a firing procedure.

In other words, the porcelain considered to be put under desired conditions at the present stage is a porcelain that does not require a condensation procedure during the buildup in which a high-degree technique is required in the preparation of a prosthesis and which is easy in handling even by a beginner. And, this porcelain is a porcelain capable of providing a prosthesis that can be seemed to be comparable to or better than a prosthesis fabricated from the conventional porcelain that is provided in powder form and is mixed with either water or the like as a temporary binder just before the use, in terms of the shape and shade. This means that not only the operability as a porcelain is improved, but also, in comparison of the quality after firing, the physical characteristic and chemical durability are comparable to or better than those of the commercially available porcelains.

The above-described points will be specifically explained below. First of all, with respect to the shade, influences (such as blackening) by a residue, such as carbon, after the firing should not be visually observed; with respect to the influences by the residue, the surface properties should not be adversely affected, and unevennesses of the surface can be visually confirmed to be equivalent to those in the conventional products; due to the matter that the condensation procedure is not employed, porosity incorporated into the porcelain during the preparation or the buildup should not be present after the firing; and, with respect to the physical characteristic, the ISO standards as international standards must be met.

Then, in order to develop a porcelain meeting the above-described requirements, the present inventors made trials and errors only for a powder of the porcelain but could not obtain a satisfactory effect for which all of the above-described requirements are met. Thus, they did something new and paid attention to a liquid for mixing the porcelain. As the liquid that can be used for such utilization, for example, Japanese Patent Laid-Open No. 101818/1995 discloses one containing a photopolymerization initiator. However, such a liquid containing a photopolymerization initiator is problematic with respect to preservative properties. This is because, in not only the case where it is preserved over a long period of time or the case where it has been subjected to irradiation with an intensive light during the preservation, but also the case where it takes a long time for the buildup, the liquid itself and the porcelain during the buildup are hardened, whereby it becomes difficult to undergo forming. Further, since the reaction is commenced upon irradiation with a light, the step becomes complicated.

On the other hand, as an attempt to ensure the operability of a porcelain without necessity for paying attention to the preservative properties of the liquid as described above, for example, Japanese Patent Laid-Open No. 199853/1986 discloses an attempt in which the porcelain is formulated into a paste-like state by using glycerin. While this attempt is proper with respect to the directionality, it has become clear that it has difficulties in homogenizing the dispersion of the porcelain powder in glycerin, coming out of an ash as a residue (e.g., residual carbon), and regulating the viscosity.

The above-described glycerin is used as a binder for formulating an opaque porcelain (sometimes simply referred to as "opaque," hereinafter) into a paste-like state, which is fused to a surface of a prosthesis made of a dental alloy to shield a metallic color of the ground. It is understood that this is low in viscosity according to the measurement results of the viscosity measured at a constant temperature of 23° C. by using a B type viscometer as described below. That is, when the revolution number is 1 rpm, the viscosity is so low that the measurement is impossible; and in the case where a conversion constant is set to be $1.61 \times 10^4$, the viscosity is 1,932 cps at 10 rpm and 4,491 cps at 100 rpm, respectively. Accordingly, in the case where such a binder is used, since the mixed porcelain does not substantially have a thixotoropic characteristics, it is hard to undergo shaping during the buildup of the porcelain.

This is because, due to the purpose of use, the opaque is intended such that it does not substantially have a thixotropy. That is, since the opaque is aimed to shield the metallic color, it is desired that the opaque is as thin as possible. This is because the opaque layer is superimposed thereon with a dentin layer, an enamel layer, a translucent layer, and the like; and from the standpoints of restrictions in the size and shape as the prosthesis, if the opaque layer is thick, these other layers must be made thin, so that the resultant shade close to a natural tooth cannot be obtained.

In addition, since the opaque as a layer is considerably thin in the thickness as compared with other layers (about 1/10 or less), the ash is liable to come out. Even when the ash remains, the opaque layer is not required to have transparency as in the enamel layer and the translucent layer, and therefore, a binder for formulating the opaque into a paste-like state can be chosen relatively freely.

SUMMARY OF THE INVENTION

The present invention is aimed to provide a paste-like porcelain that is easy in handling and preservation. That is, the porcelain according to the present invention is previously formulated into a paste-like state without necessity of a condensation procedure, so that the buildup is made easy, and simultaneously, it is completely free from incorporation of porosity; it is durable over a long period of time even in an initial state thereof; it is free from hardening occurred against the will, during the buildup of a long-span prosthesis, in which it takes a long time for the fabrication; it is easy in grasping the shade, so that even a beginner engaged can immediately manage it; and it does not substantially adversely affect a person engaged and an electric furnace for firing the porcelain.

In order to achieve the above-described aim, first of all, the present inventors made extensive and intensive investigations regarding a binder to be used for formulating a porcelain into a paste-like state. As a result, it has become clear that, when a synthetic and/or natural, hydrophilic group-containing polymeric material dissolved in one or two or more organic solvents selected from a dihydric or trihydric alcohol, a hydroxyl group-remaining ether and a hydroxy(meth)acrylate, and/or water, is used as a binder, a desired high-viscosity binder that is substantially free from changes with time can be obtained. And, it has been found that, when this binder is mixed with a porcelain powder in a predetermined ratio, a dental paste-like porcelain having highly workable consistency, that is satisfactory with the above-described aim, is obtained, leading to accomplishment of the present invention.

Specifically, the present invention relates to a dental paste-like porcelain, which comprises a mixture in a paste-like state of from 7 to 45 parts by weight of a binder comprising a synthetic and/or natural, hydrophilic group-containing polymeric material dissolved in one or two or more organic solvents selected from a dihydric or trihydric alcohol, a hydroxyl group-remaining ether and a hydroxy (meth)acrylate, and/or water and having a viscosity, as measured at a constant temperature of 23° C. and at a conversion constant of 1. $61 \times 10^4$ under the conditions that a revolution number is 1 rpm, of from 50,000 to 1,500,000 cps, and a porcelain powder as a remainder, with a total amount being 100 parts by weight.

Further, the inventors have found the following facts. That is, in the dental paste-like porcelain, when the porcelain powder to be used has a mean particle size of from 1 μm to 100 μm, not only the porcelain powder is uniformly mixed, but also no rough feeling is given to the tongue after the firing, and hence, such is preferred. Also, it is more preferred that one or two or more additives consisting of a dispersant, a surfactant, a humectant, an antiseptic, an anti-foaming agent and a lubricant are added in an amount of from 0.1 to 5 parts by weight.

DETAILED DESCRIPTION OF THE INVENTION

The dental paste-like porcelain according to the present invention is constituted by a porcelain powder and a binder with which the porcelain powder is mixed to show a paste-like state, and which comprises a synthetic and/or natural, hydrophilic group-containing polymeric material dissolved in one or two or more organic solvents selected from a dihydric or trihydric alcohol, a hydroxyl group-remaining ether and a hydroxy(meth)acrylate, and/or water.

The reason why the major component of this binder is limited to the above-described specified organic solvent(s) and/or water is as follows. That is, the dental paste-like porcelain according to the present invention is used for the buildup, similar to the conventional porcelain powders; however, if the binder is volatilized out during the porcelain application (even if the application time is long, it is within two hours), no effect is obtained as the paste-like state; and the synthetic and/or natural, hydrophilic group-containing polymeric material dissolved in a specified organic solvent (s) and/or water is efficiently decomposed and combusted.

Examples of the specified organic solvent(s) that is a major component of the binder include dihydric alcohols such as 1,2-ethanediol, 1,2-propanediol, 1,3-propanediol, 1,2-butanediol, 1,3-butanediol, 1,4-butanediol, 2,3-butanediol, 1,5-pentanediol, 2,4-pentanediol, 2-methyl-2,4-pentanediol, 3-methyl-1,5-pentanediol, 2-methyl-1,4-butanediol, 3-methyl-1,3-butanediol, and 2-methyl-1,3-propanediol; trihydric alcohols such as glycerin; hydroxyl group-remaining ethers such as diethylene glycol, triethylene glycol, tetraethylene glycol, polyethylene glycol (average molecular weight: from 200 to 600),dipropylene glycol, polypropylene glycol (average molecular weight: from 300 to 4,000), ethylene glycol monomethyl ether, ethylene glycol monoethyl ether, propylene glycol monomethyl ether, propylene glycol monoethyl ether, ethylene glycol monobutyl ether, diethylene glycolmonomethyl ether, diethylene glycolmonoethyl ether, propylene glycol monopropyl ether, dipropylene glycol monomethyl ether, tripropylene glycol monomethyl ether, diethylene glycol monobutyl ether, triethylene glycol monomethyl ether, and diglycerol; and hydroxy(meth)acrylates such as 2-hydroxyethyl acrylate, 2-hydroxyethyl methacrylate, 2-hydroxypropyl acrylate, and 2-hydroxypropyl methacrylate. They can be used singly or in admixture of two or more thereof.

The above-described organic solvents are all subjected to thermogravimetry by a pyrolysis device prior to the use, to measure a decomposition combustion temperature. The reasons for this are as follows. That is, the above-described organic solvent(s) must be wholly decomposed and combusted at a temperature of the softening point of a porcelain glass to be used as a material of the porcelain powder or lower. This is because, in the case where the softening point of the porcelain glass is lower than the decomposition combustion temperature of the organic solvent, there is fear that carbon remains in the fired porcelain, thereby making the shade grayish, or that porosity traces are generated, and hence, such is not preferred.

As the liquid as a major component of the binder, water can be used in place of the foregoing specified organic solvent, or a mixture of the foregoing specified organic solvent and water, can be used.

Examples of the synthetic and/or natural, hydrophilic group-containing polymeric material constituting the binder having a desired viscosity upon being dissolved in the foregoing specified organic solvent and/or water include poly(ammonium acrylate), poly(sodium acrylate), methyl cellulose, hydroxypropyl cellulose, hydroxypropylmethyl cellulose, hydroxyethylmethyl cellulose, hydroxyethyl cellulose, polyacrylamide, polyethylene glycol (average molecular weight: from 1,000 to 6,000), polyethylene oxide, polyvinyl alcohol, carboxymethyl cellulose, a carboxymethyl cellulose sodium salt, a carboxymethyl cellulose ammonium salt, sodium alginate, ammonium alginate, polyvinylpyrrolidone, a polyvinylpyrrolidone/vinyl acetate copolymer, a polyvinylpyrrolidone/maleic acid copolymer, an isobutylene/maleic anhydride copolymer, a methyl vinyl ether/maleic anhydride copolymer, a methyl vinyl ether/maleic anhydride ammonium salt, a methyl vinyl ether/maleic anhydride sodium salt, starch, gelatin, alginic acid, polyacrylic acid, carrageenan, locust bean gum, guar gum, gum arabic, gum tragacanth, a lignin sulfonic acid salt, curdlan, pullulan, konjak mannan, xylan, and xanthane gum.

In addition to the above-described polymeric materials, a material prepared by adding an amine, and preferably a tertiary amine, in an aqueous solution of polyacrylic acid to form a salt for neutralization, or a material prepared by dissolving the above-described synthetic and/or natural, hydrophilic group-containing polymeric material directly in water, can also be used.

With respect to such a binder, the combination and compounding ratio of the organic solvent(s) and/or water and the synthetic and/or natural, hydrophilic group-containing polymeric material may be appropriately determined. Further, needless to say, a copolymer containing these materials can also be used.

In addition, as additives to the binder, a dispersant, a surfactant, a humectant, an antiseptic, and an anti-foaming agent may be added, if desired. As the case may be, these additives may be appropriately used singly or in admixture of two or more thereof. Besides the foregoing additives, an emulsion of paraffin wax or microcrystalline wax, emulsions including an acrylic emulsions, and the like may be used as a lubricant for the addition. This lubricant can be added to the binder simultaneously with the above-described additives, and may be used singly.

An addition amount of these additives is preferably within the range of from 0.1 to 5 parts by weight based on 100 parts by weight of the total of the organic solvent an/or water and the polymeric material. This is because, when the addition amount of the additives is less than 0.1 part by weight, the effects of the additives are not obtained, whereas, when it exceeds 5 parts by weight, the viscosity is lowered depending on the combination of the additives, whereby the operability is liable to be adversely affected.

And, since such an organic solvent and/or water imparts a desired viscosity and improves the shaping properties during the buildup, it dissolves the synthetic and/or natural, hydrophilic group-containing polymeric material therein, thereby preparing a high-viscosity binder having a viscosity, as measured at a constant temperature of 23° C. and at a conversion constant of $1.61\times10^4$ under the conditions that a revolution number is 1 rpm, of from 50,000 to 1,500,000 cps. When the viscosity is less than 50,000 cps, the viscosity is too low, a dry and crumbling feeling is large, so that a good paste is not obtained. On the other hand, when it exceeds 1,500,000 cps, the viscosity of the resulting dental paste-like porcelain is too high, so that the buildup works cannot be carried out.

As the porcelain powder that is mixed with the binder, general dental porcelains that have hitherto been put on the market, such as a porcelain for metal-ceramic restorations, a porcelain for laminated veneers, and a porcelain for all ceramics, can be used without any particular restrictions.

The porcelain powder can contain a crystal. Examples of the crystal as referred to herein include leucite, potash feldspar, fluorphlogopite, diopside, mica, $\beta$-spodumene, calcium $\beta$-metaphosphate, apatite, magnesium titanate, caldiopside, tremolite, andalumina. These crystals can be used singly or in combination of two or more thereof depending on the utilization such as a porcelain for metal restorations, a porcelain for all ceramics, and a porcelain for laminated veneers.

Moreover, with respect to the glass component in the porcelain, it can be used singly or in combination of two or more thereof depending on the utilization. At this time, as already mentioned above, it should be paid attention such that, according to the thermal analysis, the softening point of the glass used as a single component or a combination of two or more components in th[0085] porcelain must be higher than the decomposition combustion temperature of the binder.

It is necessary that the porcelain powder is mixed in an amount so as to make 100 parts by weight together with from 7 to 45 parts by weight of the binder. The reasons for this are as follows. That is, when the amount of the binder is less than 7 parts by weight based on 100 parts by weight of the mixture of the binder and the porcelain powder, since the content of the porcelain powder is too high, a paste-like porcelain is too sandy whereby it becomes difficult to impart a shape; hence, such is not preferred. On the other hand, when the content of the binder exceeds 45 parts by weight, since the content of the porcelain powder is too low, a large amount of the ash remains after firing whereby the shade is liable to become gray, and fume is likely generated to a considerable extent during the firing.

The porcelain powder that is used herein preferably has a particle size of from 1 to 100 $\mu$m in terms of a mean particle size. The reasons for this are as follows. That is, when the mean particle size of the porcelain powder exceeds 100 $\mu$m, a rough feelings is remarkable, and the operability is so poor that it is difficult to carry out the buildup. On the other hand, when it is less than 1 $\mu$m, a transparent feeling of the surface (porcelain) of the resulting prosthesis is impaired, and hence, such is not preferred. In this case, in the case where the operability during the buildup is important, when the mean particle size of the porcelain powder is within the range of from 7 to 50 μm, the buildup is relatively easy, and hence, such is more preferred.

The dental paste-like porcelain according to the present invention, as prepared so as to meet the various requirements described above, when used as a porcelain for metal restorations, can be used for not only a dentin which is used as a body, an enamel, and a translucent porcelain, but also an opacifieddentin, a cervical dentin, and a margin porcelain.

The dental paste-like porcelain according to the present invention is specifically explained below with reference to the following Examples, but it should not be construed that the invention is limited thereto.

The firing conditions, viscosity measurement, strength and shade as well as the evaluations of surface smoothness and operability set forth in the Examples are as follows.

(1) Firing Conditions:

A paste-like porcelain comprising a mixture of a porcelain powder and a binder was filled into a predetermined mold to prepare a specimen. Using a porcelain furnace (a trade name: CERAMIMAT FA-IV, manufactured by GC Corporation), this specimen was subjected to firing in vacuity of a drying step in which the firing furnace having an internal temperature of 600° C. is descended from a predetermined position to a position where the specimen is placed on a firing table on mai[008e] body of the apparatus over 10 minutes, and after close contact between the firing furnace and the main body of the apparatus, the specimen is engaged at that temperature for 2 minutes; a heating step in which at the final stage of the drying step, the specimen is heated at a temperature climbing rate of 50° C./min in a state that the specimen is completely accommodated in the furnace in a sealed (vacuum) state; and an engaging step in which after the temperature has reached a firing temperature as previously estimated depending on the composition of the porcelain powder, the specimen is engaged at that temperature for one minute, and then, the supply of an electric power to the firing furnace is stopped. Thereafter, in a state that the specimen was placed on the firing table, the specimen was cooled while elevating the firing furnace to which the supply of the electric power had been stopped to a predetermined position over 2 minutes.

(2) Measurement of Viscosity of the Binder:

In a constant-temperature atmosphere at 23° C., a binder was filled into a mold. Five minutes after the start of revolution at a revolution number of 1 rpm by a B type viscometer (a trade name: B8U Type, manufactured by TOKIMEC Inc.), an indicated value (scale) on an indicating panel was read, and a measurement value as measured at a conversion constant of $1.61 \times 10^4$ was substituted into the following equation to obtain a viscosity of the binder.

Viscosity=(Measurement value)×[(Conversion constant) $(1.61 \times 10^4)$]/(Revolution number)

(3) Bending Strength:

A paste-like porcelain comprising a mixture of a porcelain powder and a binder was filled into a mold having a size of 5 mm×2 mm×25 mm to prepare a specimen. The specimen was fired under the same conditions as the firing conditions in (1) above. Thereafter, the specimen was cooled and taken out from the mold, and then roughly polished under pouring with water using an SiC waterproof polishing paper of 38 μm into a plate form having a size of 4 mm×1.2 mm×22 mm, a surface of which was further subjected to finish polishing under pouring with water using an SiC waterproof polishing paper of 15 μm, to provide a test sample. Using a universal testing machine (a trade name: Autograph, manufactured by Shimadzu Corporation), this test sample was measured for three-point bending strength at a distance of supports of 15 mm and at a cross head speed of 1 mm/min.

(4) Shade:

The shade of a fired porcelain was evaluated by measuring the transparency. A paste-like porcelain comprising a mixture of a porcelain powder and a binder was filled into a predetermined mold to prepare a specimen. The specimen was then fired under the same conditions as the firing conditions in (1) above. Thereafter, the specimen was formed by roughly polishing under pouring with water using an SiC waterproof polishing paper of 38 μm and further subjected to surface polishing under pouring with water using an SiC waterproof polishing paper of 15 μm, to prepare a disc-like sample having a thickness of 1 mm and a diameter of 10 mm. A surface of the sample was subjected to mirror like polishing under pouring with water using an SiC waterproof polishing paper of 3.75 μm to provide a test sample. The test sample was measured for a Y value as one of the three stimulation values using a spectrophotometer (a trade name: PR-650, manufactured by Minolta Co., Ltd.). A YW value as a measurement value when a white standard board was used as a background of the sample (hereinafter simply referred to as "YW value") and a YB value as a measurement value when a black standard board was used as a background of the sample (hereinafter simply referred to as "YB value") were each measured, and a contrast ratio was obtained according to the following equation.

Contrast ratio=(YB value)/(YW value)

Then, using the contrast value obtained in the above equation, the transparency was calculated according to the following equation.

Transparency=1-(Contrast ratio)=1 (YB value)/(YW value)

The transparency is a numerical value varying within the range of from 0 to 1, and the higher the value, the higher the transparency is. Accordingly, in the case where the content of the remaining ash in the porcelain after the firing is high, that value becomes smaller.

(5) Smoothness:

A paste-like porcelain comprising a mixture of a porcelain powder and a binder was filled into a mold having a diameter of 20 mm and a thickness of 2 mm to prepare a specimen. The specimen was fired under the same conditions as the firing conditions in (1) above. Thereafter, a surface of the specimen was roughly polished under pouring with water using an SiC waterproof polishing paper of 38 μm and further subjected to finish polishing under pouring with water using an SiC waterproof polishing paper of 15 μm, to provide a test sample. Also, a translucent T2 (a trade name: G-CERA ORBIT, manufactured by GC Corporation) that is a commercially available porcelain was filled as a standard sample into the above-described mold (diameter: 20 mm, thickness: 2 mm) by the condensation method to prepare a specimen. This specimen was subjected to surface polishing in the same procedures as in the above-mentioned specimen (test sample) to provide a standard sample. Both the test sample and the standard sample were visually observed to confirm the number of surface porosity.

The evaluation was made in the following criteria based on the standard sample.

C: The number of porosity on the surface of the test sample is higher.
B: The number of porosity is equal.
A: The number of porosity is lower.
(6) Operability:

An opaque OA3 (a trade name: G-CERA ORBIT, manufactured by GC Corporation) as a commercial available porcelain for metal restorations was filled into a mold in an approximately quadrangular pyramid form having a diameter of 8 mm and a height of 6 mm by the condensation method to prepare a specimen, which was then fired under predetermined firing conditions to obtain an opaque. Next, a paste-like porcelain comprising a mixture of a porcelain powder and a binder was applied on the thus obtained opaque, thereby evaluating the buildup operability.

The evaluation of the operability was made in the following criteria.
C: During the buildup, a sag of the porcelain was generated, or a drying and crumbling phenomenon or cracking was generated, so that it was difficult to perform shaping.
A: The phenomena set forth above were not observed.

EXAMPLE 1

Preparation of Porcelain Powder

In a mortar were mixed 53 parts by weight of feldspar, 28 parts by weight of silica, 6 parts by weight of alumina, 18 parts by weight of potassium hydrogencarbonate, 7parts by weight of sodium carbonate, 0.1 part by weight of magnesium carbonate, and 1 part by weight of calcium carbonate, and the mixture was melted in an electric furnace to prepare a homogenous glass. The glass was ground by a ball mill to obtain a coarse powder. The coarse powder was crystallized in an electric furnace kept at a predetermined temperature to deposit a leucite crystal. And the glass containing this crystal was again ground in the ball mill, and the resulting coarse powder was sieved to obtain a porcelain powder having a mean particle size of 10 μm and a softening point of 700° C.

Preparation of Binder

To 97.5 parts by weight of distilled water was gradually added 2.5 parts by weight of poly(ammonium acrylate), and the mixture was stirred in a homomixer set up at 3,500 rpm for 40 minutes to obtain a binder. This binder had a viscosity of 552,000 cps.

Preparation of the Dental paste-like Porcelain

In a constant-temperature atmosphere at 23° C., the porcelain powder (71 parts by weight) and the binder (29 parts by weight) as prepared above were mixed in a mortar using a spatula for about 20 minutes to obtain a paste-like porcelain.

EXAMPLE 2

Preparation of Binder

To 97 parts by weight of distilled water was gradually added 3 parts by weight of guar gum, and the mixture was stirred in a homomixer set up at 3,500 rpm for 40 minutes to obtain a binder. This binder had a viscosity of 338,000 cps.

Preparation of the Dental Paste-like Porcelain

The thus obtained binder (26 parts by weight) and 74 parts by weight of the porcelain powder of Example 1 were mixed under the same conditions as in Example 1 to obtain a paste-like porcelain.

EXAMPLE 3

Preparation of Binder

To 97 parts by weight of distilled water was gradually added 3 parts by weight of guar gum, and further added 2 parts by weight of a 50% hyaluronic acid aqueous solution as a humectant. Thereafter, the mixture was stirred in a homomixer set up at 3,500 rpm for 40 minutes to obtain a binder. This binder had a viscosity of 301,000 cps.

Preparation of the Dental paste-like Porcelain

The thus obtained binder (26 parts by weight) and 74 parts by weight of the porcelain powder of Example 1 were mixed under the same conditions as in Example 1 to obtain a paste-like porcelain.

This paste-like porcelain is one prepared by adding 2parts by weight of 50% hyaluronic acid aqueous as a humectant to the binder in the paste-like porcelain of Example 2 and exhibited a good moisture retention during the buildup works. Further, this paste-like porcelain was slightly superior to the paste-like porcelain of Example 2 in the buildup works of a prosthesis requiring a considerable time, such as a long-span bridge.

EXAMPLE 4

Preparation of Binder

To 30 parts by weight of distilled water was gradually added 1 part by weight of 1,3-propanediol. Thereafter, 3 parts by weight of polyacrylic acid and part by weight of ethanolamine were gradually added to 65 parts by weight of distilled water. The both solutions were stirred in a homomixer set up at 3, 500 rpm for 40 minutes to obtain a binder. This binder had a viscosity of 371,000 cps.

Preparation of the Dental Paste-like Porcelain

The thus obtained binder (25 parts by weight) and 75parts by weight of the porcelain powder of Example 1 were mixed under the same conditions as in Example 1 to obtain a paste-like porcelain.

EXAMPLE 5

Preparation of Binder

To a mixed solution of 80 parts by weight of polyethylene glycol (average molecular weight: 200) and 5 parts by weight of 1,2-ethanediol were gradually added 13 parts by weight of hydroxypropylmethyl cellulose and 2 parts by weight of hydroxyethyl cellulose, and the mixture was stirred in a homomixer set up at 3,500 rpm for 40 minutes to obtain a binder. This binder had a viscosity of 816,000 cps.

Preparation of the Dental Paste-like Porcelain

The thus obtained binder (27 parts by weight) and 73 parts by weight of the porcelain powder of Example 1 were mixed under the same conditions as in Example 1 to obtain a paste-like porcelain.

EXAMPLE 6

Preparation of Binder

To a mixed solution of 80 parts by weight of polyethylene glycol (average molecular weight: 200), 3 parts by weight of 1,2-propanediol and 2 parts by weight of 2-hydroxypropyl methacrylate were gradually added 15 parts by weight of hydroxypropylmethyl cellulose, and the mixture was stirred in a homomixer setup at 3,500 rpm for 40 minutes to obtain a binder.

This binder had a viscosity of 583,000 cps.

Preparation of the Dental Paste-like Porcelain

The thus obtained binder (24 parts by weight) and 76 parts by weight of the porcelain powder of Example 1 were mixed under the same conditions as in Example 1 to obtain a paste-like porcelain.

EXAMPLE 7

Preparation of Binder

To a mixed solution of 80 parts by weight of polyethylene glycol (average molecular weight: 200), 3 parts by weight of 1,2-propanediol and 2 parts by weight of 2-hydroxypropyl methacrylate were gradually added 15 parts by weight of hydroxypropylmethyl cellulose and 1 part by weight of a wax emulsion as a lubricant, and the mixture was stirred in a homomixer set up at 3,500 rpm for 40 minutes to obtain a binder. This binder had a viscosity of 439,000 cps.

Preparation of the Dental Paste-like Porcelain

The thus obtained binder (24 parts by weight) and 76 parts by weight of the porcelain powder of Example 1 were mixed under the same conditions as in Example 1 to obtain a paste-like porcelain.

This paste-like porcelain is one prepared by adding 1 part by weight of the wax emulsion as a lubricant to the binder in the paste-like porcelain of Example 6. This paste-like porcelain was relieved in stickiness to a spatula used as an buildup instrument as compared with the paste-like porcelain of Example 6 and therefore, was superior in operability.

EXAMPLE 8

Preparation of Binder

To a mixed solution of 80 parts by weight of 1,3-butanediol and 2 parts by weight of polyethylene glycol (average molecular weight: 200) were gradually added 3 parts by weight of hydroxyethyl cellulose and 15 parts by weight of hydroxypropyl cellulose, and the mixture was stirred in a homomixer set up at 3,500 rpm for 40 minutes to obtain a binder. This binder had a viscosity of 688,000 cps.

Preparation of the Dental Paste-like Porcelain

The thus obtained binder (28 parts by weight) and 72 parts by weight of the porcelain powder of Example 1 were mixed under the same conditions as in Example 1 to obtain a paste-like porcelain.

EXAMPLE 9

Preparation of Binder

To a mixed solution of 65 parts by weight of 1,3-butanediol and 17 parts by weight of 2-hydroxyethyl methacrylate were gradually added 8 parts by weight of polyvinylpyrrolidone, 8 parts by weight of hydroxypropyl cellulose and 2 parts by weight of hydroxypropylmethyl cellulose, and the mixture was stirred in a homomixer set up at 3,500 rpm for; 40 minutes to obtain a binder. This binder had a viscosity of 780,000 cps.

Preparation of the Dental Paste-like Porcelain

The thus obtained binder (28 parts by weight) and 72 parts by weight of the porcelain powder of Example 1 were mixed under the same conditions as in Example 1 to obtain a paste-like porcelain.

EXAMPLE 10

Preparation of Binder

To a mixed solution of 75 parts by weight of 1,2-ethanediol, 5 parts by weight of 1,3-butanediol and 5 parts by weight of polyethylene glycol (average molecular weight: 200) were gradually added 10 parts by weight of polyvinylpyrrolidone and 5 parts by weight of hydroxypropylmethyl cellulose, and the mixture was stirred in a homomixer set up at 3,500 rpm for 40 minutes to obtain a binder. This binder had a viscosity of 415,000 cps.

Preparation of the Dental Paste-like Porcelain

The thus obtained binder (24 parts by weight) and 76 parts by weight of the porcelain powder of Example 1 were mixed under the same conditions as in Example 1 to obtain a paste-like porcelain.

EXAMPLE 11

Preparation of Binder

To 80 parts by weight of 1,3-butanediol was gradually added 15 parts by weight of polyvinylpyrrolidone and 5 parts by weight of hydroxypropylmethyl cellulose, and the mixture was stirred in a homomixer set up at 3,500 rpm for 40 minutes to obtain a binder. This binder had a viscosity of 725,000 cps.

Preparation of the Dental Paste-like Porcelain

The thus obtained binder (27 parts by weight) and 73 parts by weight of the porcelain powder of Example 1 were mixed under the same conditions as in Example 1 to obtain a paste-like porcelain.

EXAMPLE 12

Preparation of Binder

To 87 parts by weight of 1,3-propanediol was gradually added 13 parts by weight of hydroxypropylmethyl cellulose, and the mixture was stirred in a homomixer set up at 3,500 rpm for 40 minutes to obtain a binder. This binder had a viscosity of 499,000 cps.

Preparation of the Dental Paste-like Porcelain

The thus obtained binder (28 parts by weight) and 72 parts by weight of the porcelain powder of Example 1 were mixed under the same conditions as in Example 1 to obtain a paste-like porcelain.

EXAMPLE 13

Preparation of Binder

To a mixed solution of 97 parts by weight of distilled water and 0.5 parts by weight of 1,2-ethanediol were gradually added 2.5 parts by weight of poly(ammonium acrylate), and the mixture was stirred in a homomixer set up at 3,500 rpm for 40 minutes to obtain a binder. This binder had a viscosity of 397,000 cps.

Preparation of the Dental Paste-like Porcelain

The thus obtained binder (29 parts by weight) and 71 parts by weight of the porcelain powder of Example 1 were mixed under the same conditions as in Example 1 to obtain a paste-like porcelain.

EXAMPLE 14

Preparation of Binder

To 81 parts by weight of 2-hydroxyethyl methacrylate was gradually added 5 parts by weight of hydroxypropylmethyl cellulose, 4 parts by weight of hydroxyethyl cellulose and 10 parts by weight of hydroxypropyl cellulose, and the mixture was stirred in a homomixer set up at 3,500 rpm for 40 minutes to obtain a binder. This binder had a viscosity of 435,000 cps.

Preparation of the Dental Paste-like Porcelain

The thus obtained binder (25 parts by weight) and 75 parts by weight of the porcelain powder of Example 1 were mixed under the same conditions as in Example 1 to obtain a paste-like porcelain.

EXAMPLE 15

Preparation of Binder

To a mixed solution of 80 parts by weight of polyethylene glycol (average molecular weight: 200) and 5 parts by weight of 1,2-ethanediol were gradually added 8 parts by weight of hydroxypropylmethyl cellulose and 7 parts by weight of a 15° C. methyl vinyl ether/maleic anhydride ammonium aqueous solution, and the mixture was stirred in a homomixer set up at 3,500 rpm for 40 minutes to obtain a binder. This binder had a viscosity of 383,000 cps.

Preparation of the Dental Paste-like Porcelain

The thus obtained binder (27 parts by weight) and 73 parts by weight of the porcelain powder of Example 1 were mixed under the same conditions as in Example 1 to obtain a paste-like porcelain.

COMPARATIVE EXAMPLE 1

Preparation of Binder

To 97 parts by weight of distilled water was gradually added 3 parts by weight of methyl cellulose, and the mixture was stirred in a homomixer set up at 3,500 rpm for 20 minutes to obtain a binder. This binder had a viscosity of 12,000 cps.

Preparation of the Dental Paste-like Porcelain

The thus obtained binder (25 parts by weight) and 75 parts by weight of the porcelain powder of Example 1 were mixed under the same conditions as in Example 1 to obtain a paste-like porcelain.

This paste-like porcelain was large in the dry and crumbling feeling and therefore, was remarkably inferior in the operability as compared with those of Examples 1 to 15.

COMPARATIVE EXAMPLE 2

Preparation of Binder

To 95 parts by weight of distilled water was gradually added 3 parts by weight of polyvinyl alcohol and 2 parts by weight o[0086] polyethylene oxide, and the mixture was stirred in a homomixer set up at 3,500 rpm for 20 minutes to obtain a binder. This binder had a viscosity of 26,000 cps.

Preparation of the Dental Paste-like Porcelain

The thus obtained binder (25 parts by weight) and 75 parts by weight of the porcelain powder of Example 1 were mixed under the same conditions as in Example 1 to obtain a paste-like porcelain.

This paste-like porcelain was large in the dry and crumbling feeling and therefore, was remarkably inferior in the operability as compared with those of Examples 1 to 15.

COMPARATIVE EXAMPLE 3

Preparation of Binder

To 80 parts by weight of distilled water was gradually added 10 parts by weight of guar gum and 10 parts by weight of carboxymethyl cellulose, and the mixture was stirred in a homomixer set up at 3,500 rpm for 40 minutes to obtain a binder.

This binder had a viscosity of 423,000 cps.

Preparation of the Dental Paste-like Porcelain

The thus obtained binder (50 parts by weight) and 50 parts by weight of the porcelain powder of Example 1 were mixed under the same conditions as in Example 1 to obtain a paste-like porcelain.

Since this paste-like porcelain was so large in generation of a sag, it was difficult to impart a fine shape. Therefore, the paste-like porcelain was remarkably inferior in the operability as compared with those of Examples 1 to 15.

COMPARATIVE EXAMPLE 4

Preparation of the Dental Paste-like Porcelain

Polyethylene glycol (average molecular weight: 400) (35 parts by weight) as a binder and 65 parts by weight of the porcelain powder of Example 1 were mixed under the same conditions as in Example 1 to obtain a paste-like porcelain.

Since this paste-like porcelain did not at all show any ductility, it was difficult to impart a shape. Therefore, the paste-like porcelain was remarkably inferior in the operability as compared with those of Examples 1 to 15.

COMPARATIVE EXAMPLE 5

Preparation of the Dental Paste-like Porcelain

Water (30 parts by weight) as a binder and 70 parts by weight of the porcelain powder of Example 1 were mixed under the same conditions as in Example 1 to obtain a paste-like porcelain. Thereafter, the mixture was subjected to condensation in the customary manner. However, during this procedure, it was necessary to remove an excess of water. Therefore, the paste-like porcelain was remarkably inferior in the operability as compared with those of Examples 1 to 15.

The molds used in the respective Examples and Comparative Examples are common, and the firing conditions are identical. The results obtained in these Examples and Comparative Examples are summarized and shown in Table 1.

TABLE 1

|  | Bending strength (Mpa) | Shade | Smoothness | Operability |
| --- | --- | --- | --- | --- |
| Example 1 | 85 | 0.88 | A | A |
| Example 2 | 90 | 0.78 | A | A |
| Example 3 | 86 | 0.79 | A | A |
| Example 4 | 88 | 0.78 | A | A |
| Example 5 | 85 | 0.80 | A | A |
| Example 6 | 82 | 0.85 | A | A |
| Example 7 | 84 | 0.81 | A | A |
| Example 8 | 81 | 0.79 | B | A |
| Example 9 | 81 | 0.77 | B | A |
| Example 10 | 83 | 0.78 | A | A |
| Example 11 | 82 | 0.78 | A | A |
| Example 12 | 84 | 0.84 | A | A |
| Example 13 | 86 | 0.83 | A | A |
| Example 14 | 85 | 0.79 | A | A |
| Example 15 | 87 | 0.82 | A | A |
| Comparative Example 1 | 58 | 0.62 | C | C |
| Comparative Example 2 | 69 | 0.71 | B | C |
| Comparative Example 3 | 45 | 0.33 | C | C |
| Comparative Example 4 | 70 | 0.72 | B | C |
| Comparative Example 5 | 81 | 0.77 | B | C |

As described above, since in the dental paste-like porcelain according to the present invention, the porcelain and the binder are previously mixed, it can be provided in a state that porosity are not incorporated at all. Further, it can be used directly without subjecting to condensation every time of use. Moreover, in the case where a large-sized prosthesis such as a long-span bridge is fabricated, it can be easily applied into a desired form within a short period of time because it is free from drying and hardening, or deformation during the procedure.

In addition to this, since it is not the case that the porcelain powder and the liquid such as water are mixed one by one at the time of use, a porcelain mixed under a definite condition can be always obtained, and the shade of the porcelain after firing can be easily grasped. Further, the strength and shade of the final porcelain obtained from the dental paste-like porcelain according to the present invention are quite comparable to those of the commercially available porcelains. Moreover, in the dental paste-like porcelain according to the present invention, it is possible to greatly reduce the costs needed in the fabricated of a prosthesis including shortening of the working time of a person engaged, and it is easy to preserve the dental paste-like porcelain over a long period of time.

Also, since the dental paste-like porcelain according to the present invention does not require an special training for the skill, it can be conveniently used in the same procedure as in the case where a hard resin is applied. Accordingly, even a beginner can easily manage it.

In the light of the above, the dental paste-like porcelain according to the present invention having such effects is very valuable in contributing to the dental remedy.

While the present invention has been described in detail and with reference to specific embodiments thereof, it will be apparent to one skilled in the art that various changes and modifications can be made therein without departing from the spirit and scope thereof.

What is claimed is:

1. A dental porcelain paste comprising a mixture in a paste-like state of from 7 to 45 parts by weight of a binder comprising a synthetic and/or natural, hydrophilic group-containing polymeric material dissolved in at least one solvent selected from the group consisting of a dihydric alcohol, a trihydric alcohol, a hydroxyl group-containing ether, a hydroxy(meth)acrylate water and mixtures thereof, and having a viscosity, as measured at a constant temperature of 23° C. and at a conversion constant of $1.61 \times 10^4$ under the conditions that a revolution number is 1 rpm, of from 50,000 to 1,500,000 cps, and a porcelain powder as a remainder, with a total amount being 100 parts by weight.

2. The dental porcelain past claimed in claim 1, wherein the porcelain powder has a mean particle size of from 1 $\mu$m to 100 $\mu$m.

3. The dental porcelain paste as claimed in claim 1 further comprising from 0.1 to 5 parts by weight of at least one additive selected from the group consisting of a dispersant, a surfactant, a humectant, an antiseptic, an anti-foaming agent and a lubricant.

4. The dental porcelain paste as claimed in claim 3, wherein said humectant is hyaluronic acid.

5. The dental porcelain paste as claimed in claim 3, wherein the lubricant is a wax emulsion.

6. The dental porcelain paste as claimed in claim 1, wherein the dihydric alcohol is selected from the group consisting of 1,2-ethanol, 1,2-propanediol, 1,3-propanediol, 1,2-butanediol, 1,3-butanediol, 1,4-butanediol, 2,3-butanediol, 1,5-pentanediol, 2,4-pentanediol, 2-methyl-2,4-pentanediol, 3-methyl-1,5-pentanediol, 2-methyl-1,4-butanediol, 3-methyl-1,3-butanediol, and 2-methyl-1,3-propanediol.

7. The dental porcelain paste as claimed in claim 1, wherein the trihydric alcohol is selected from the group consisting of diethylene glycol, triethylene glycol, tetraethylene glycol, polyethylene glycol, dipropylene glycol, polypropylene glycol, ethylene glycol monomethyl ether, ethylene glycol monoethyl ether, propylene glycol monomethyl ether, propylene glycol monoethyl ether, ethylene glycol monobutyl ether, diethylene glycol monomethyl ether, diethylene glycol monoethyl ether, propylene glycol monopropyl ether, dipropylene glycol monomethyl ether, tripropylene glycol monomethyl ether, diethylene glycol monobutyl ether, triethylene glycol monoether and diglycerol.

8. The dental porcelain paste as claimed in claim 1, wherein the hydroxy (meth)acrylate is selected from the group consisting of 2-hydroxyethyl acrylate, 2-hydroxyethyl methacrylate, 2-hyroxypropyl acrylate, and 2-hydroxypropyl methacrylate.

9. The dental porcelain paste as claimed in claim 1, further comprising a material prepared by adding an amine to an aqueous solution of polyacrylic acid.

10. A dental porcelain paste comprising a mixture of from 7 to 45 parts by weight of a binder comprising a synthetic and/or natural, hydrophilic group-containing polymeric material dissolved in a solvent selected from the group consisting of a dihydric alcohol, a trihydric alcohol, a hydroxyl group-containing ether, a hydroxy(meth)acrylate, water and mixtures thereof, said binder having a viscosity, as measured at a constant temperature of 23° C. and at a conversion constant of $1.61 \times 10^4$ under the conditions that a revolution number is 1 rpm, of from 50,000 to 1,500,000 cps, and a porcelain powder as a remainder, with a total amount being 100 parts by weight, and from 0.1 to 5 parts by weight of at least one additive selected from the group consisting of a dispersant, a surfactant, a humectant, an antiseptic, an anti-foaming agent, a lubricant and mixtures thereof, wherein the porcelain powder has a mean particle size of from 1 $\mu$m to 100 $\mu$m.

* * * * *